(12) United States Patent
Debregeas et al.

(10) Patent No.: US 6,458,389 B1
(45) Date of Patent: Oct. 1, 2002

(54) MICROGRANULES CONTAINING CISPLATIN

(75) Inventors: Patrice Debregeas, Paris; Gérard Leduc, Malesherbes; Pascal Oury, Paris; Pascal Suplie, Montaure, all of (FR)

(73) Assignee: Laboratoires Des Produits Ethiques Ethypharm, Houdan (FR)

( * ) Notice: Subject to any disclaimer, the term of this patent is extended or adjusted under 35 U.S.C. 154(b) by 0 days.

(21) Appl. No.: 09/367,270

(22) PCT Filed: Feb. 10, 1998

(86) PCT No.: PCT/FR98/00251

§ 371 (c)(1),
(2), (4) Date: Sep. 8, 1999

(87) PCT Pub. No.: WO98/34599

PCT Pub. Date: Aug. 13, 1998

(30) Foreign Application Priority Data

Feb. 11, 1997 (FR) .............................................. 97 01545

(51) Int. Cl.⁷ .............................. A61K 9/16; A61K 9/50
(52) U.S. Cl. ...................... 424/490; 424/489; 424/493; 424/494; 424/497
(58) Field of Search ............................... 424/489, 490, 424/491, 494, 497, 493

(56) References Cited

U.S. PATENT DOCUMENTS

| | | | | |
|---|---|---|---|---|
| 4,925,674 A | * | 5/1990 | Giannini et al. | 424/469 |
| 5,795,882 A | * | 8/1998 | Bishop et al. | 514/170 |
| 5,945,122 A | * | 8/1999 | Abra et al. | 424/450 |

FOREIGN PATENT DOCUMENTS

| | | |
|---|---|---|
| DE | 35 23 454 | 1/1987 |
| EP | 059817 A1 * | 3/1981 |
| EP | 0 167 825 | 1/1986 |
| WO | 96 27346 | 9/1996 |

* cited by examiner

*Primary Examiner*—Thurman K. Page
*Assistant Examiner*—Liliana Di Nola-Baron
(74) *Attorney, Agent, or Firm*—Foley & Lardner

(57) ABSTRACT

The invention concerns an oral formulation of cisplatin, in the form of controlled-release microgranules, and its method of formulation by grossing in an aqueous medium. The invention also concerns a pharmaceutical preparation containing controlled-release cisplatin microgranules, optionally combined with an anticancer agent, to be used in anticancer therapy. The invention further provides a use for these microgranules for making orally administered medicaments for polychemotherapy or in combination with radiotherapy.

30 Claims, 1 Drawing Sheet

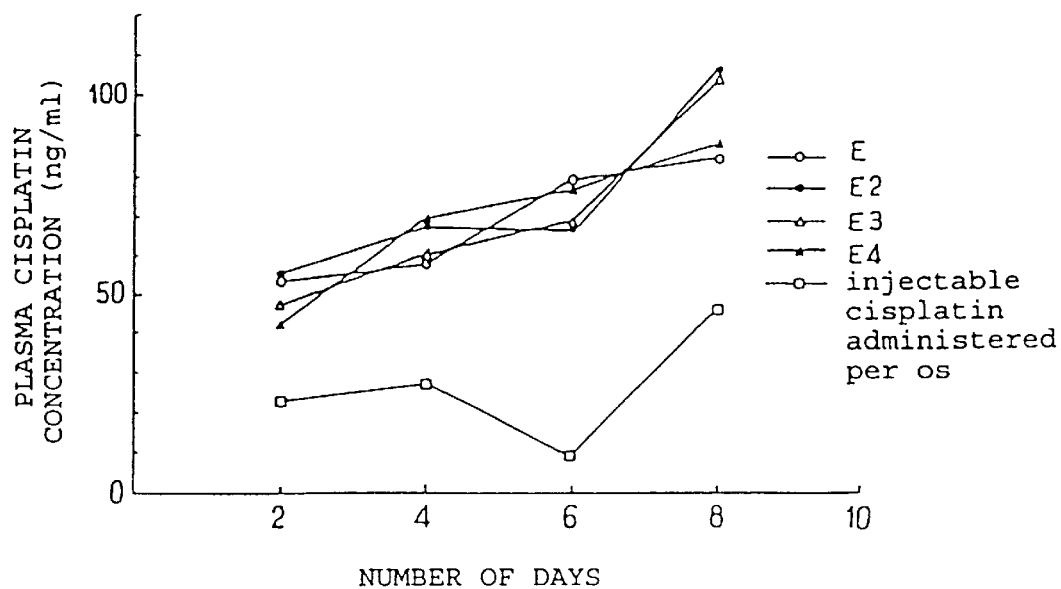
FIG_1
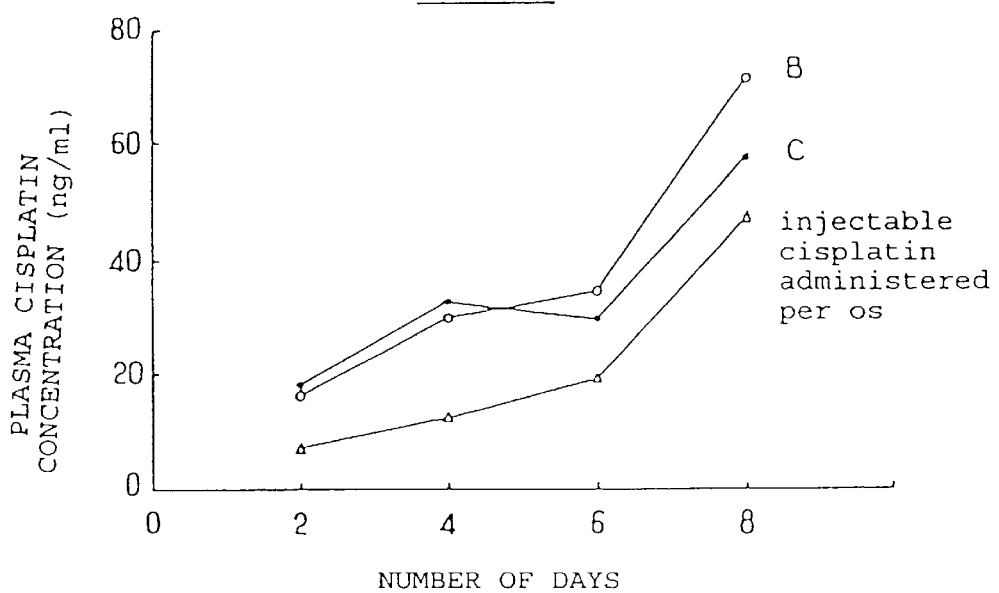
FIG_2

MICROGRANULES CONTAINING CISPLATIN

The present invention relates to a cisplatin formulation for oral administration.

Cisplatin is an anticancer agent known for its effectiveness but also for its significant side effects observed when it is administered intravenously, in particular: nephrotoxicity, gastrointestinal toxicity (nausea, vomiting), neurotoxicity and moderate myelo-suppression.

The nephrotoxicity induced by cisplatin can be alleviated by intravenous saline hydration and by diuresis.

For the last twenty-five years, research has been carried out on cisplatin analogues. Only twelve of these analogues have been evaluated in clinical trials: some have proved to be even more toxic than cisplatin and none has shown an anticancer activity superior to cisplatin.

Researchers have thus turned towards the study of the reduction in toxicity of cisplatin rather than towards that of new analogues.

A first line of research relates to the oral administration of cisplatin in animals.

Studies carried out by Siddik Z. H. et al. and presented at the 74th Congress of the American Cancer Research Association in March 1984 allowed the anticancer activity of cisplatin administered by the oral route in mice affected by plasmacytoma ADJ/PLA to be evaluated. The plasma platinum concentration reached a peak of 4.3 μg/ml after 30–60 minutes for a dose of 50 mg/kg. The bioavailability in the mouse was 31–36% and the incidence of nephrotoxicity was only 20%.

Hasegawa Y. et al. confirm with respect to Muridae, in Chem. Pharm. Bull., 33(12), 5511–5514, 1985, that cisplatin passes into the blood after oral administration and that it is effective under these conditions against solid tumours.

Binks S. P. et al. demonstrate, in Biochemical Society Transactions, 616th Meeting, London, 14, 694 (1986), that the absorption of cisplatin after oral administration is so rapid that the plasma platinum concentration reaches its maximum in less than two hours. The highest levels of platinum are observed in the kidneys.

Analysis with an electron microscope of tissues excised 48 hours after oral administration of cisplatin reveals only slight changes in the kidneys, whereas, for an intravenous administration, symptoms of nephrotoxicity are observable.

Borch R. F. et al. have shown, in Proc. Natl. Acad. Sci., USA, 76, 6611–6614, that urea concentrations in the blood were multiplied by 14 in rats receiving the maximum tolerated dose of cisplatin via the intravenous route and then this result was confirmed by another study by Morgan S. E. et al. (Pharmacology Communication, 1993, Vol. 3, No. 1, 9–18) and shows that administration by the oral route can greatly decrease the nephrotoxicity of cisplatin. No histopathological change in the kidneys was observed in mice treated orally with a toxic dose of cisplatin of 70 mg/kg.

Howell S. B., in Plenum Press, New York. p. 93 (1991), and Harrap K. R. et al., in Adv. Enzyme Regul., 31 (31), 1991, show that the degree of activity of cisplatin administered by the oral route is less than that obtained by the parenteral route and that higher doses are necessary for an oral administration because of the relatively low bioavailability of cisplatin in this case. Consequently, no clinical trial has been carried out on man because the bioavailability of cisplatin administered by the oral route was too low in comparison with conventional intravenous formulations.

A second line of research relates to the combination of low doses of cisplatin with other therapeutic methods.

T. Shirasaka has provided, in Cancer Chemother. Pharmacol., 32, 167–172 (1993) and in Jpn. J. Cancer Chemother., 2/(7), 1025–1028 (1994), a therapy which consists in combining the administration of 5-fluorouracil and low-dose cisplatin. He suggests a therapy of four weeks, which consists in administering a perfusion of 5-fluorouracil in combination with an intravenous dose of 5–6 mg/day of cisplatin.

The anticancer effectiveness of this therapy on the solid tumours of the rodents studied is superior to that of 5-fluorouracil alone or of cisplatin alone and its toxicity is lower.

Many studies carried out in Japan have shown that, with a low-dose regimen, cisplatin in combination with 5-fluorouracil is effective in the treatment of various cancers; moreover, its toxicity is reduced. It is then no longer necessary to resort to hydration by an intravenous route in order to prevent nephrotoxicity.

Moreover, it has been demonstrated, in Chemotherapy, 1996, Vol/Iss/Pg 42/6 (452–458), that low-dose cisplatin can also be combined with S1, an antitumour medicament of oral form which is a tegafur/5-chloro-2,4-dihydroxypyridine/oxonic acid mixture in a 1/0.4/1 molar proportion discovered by T. Shirasaka.

Other combinations of low-dose cisplatin are also possible with other anticancers, such as, but not restricted to, the combination of vinblastine with bleomycin, the combination of etoposide with bleomycin, or alternatively paclitaxel.

In addition, Ducreux M. et al., in Annals of Oncology, 5 (Suppl 8), 81 (1994), have shown that the combination of radiotherapy and of an administration of 4–6 mg/m$^2$/day of cisplatin by the intravenous route for 4–6 weeks improves the anticancer activity and reduces the side effects.

There currently exists no oral cisplatin formulation and the object of the present invention is to provide controlled-release microgranules for oral administration containing cisplatin, the mean particle size of which is between 0.4 and 1.5 mm, in particular between 1 and 1.25 mm.

Controlled release is understood to mean an instantaneous release, a release sustained over time or alternatively a release with targeting of the absorption site, in particular at the ileum where the pH is of the order of 7.

This formulation advantageously provides a bioavailability superior to that of cisplatin of injectable form administered orally and an acceptable gastrointestinal toxicity.

After an intravenous administration, the plasma platinum concentration increases and then decreases rapidly, which leads to significant fluctuations in concentration and causes periods of therapeutic under-and over-concentration responsible for nephrotoxicity and nausea/vomiting.

The controlled-release microgranules formulation according to the invention advantageously makes it possible to release the active principle more evenly and to avoid plasma peaks while maintaining a blood level which is sufficiently high to produce the desired therapeutic effect, without, however, reaching toxic levels which can cause side effects for the patient, because of the extensive distribution of the granules along the digestive tract.

The formulation according to the invention also makes it possible to keep the plasma concentration constant over a longer period of time and to decrease the variations between and within individuals by virtue of a high exchange surface area and avoids the release of a large amount of active principle localized at one point of the digestive mucous membrane.

An advantage of the oral form according to the invention is that it can be used by the patient himself in his home; thus, the patient no longer has to resort to frequent intravenous administrations in a hospital which require professional assistance. Moreover, for hospitalized patients, the oral form according to the invention improves the quality of life by reducing the time spent in hospital and by freeing them from painful treatments, in particular in the case of perfusions at the rate of 100 hours/week.

Each microgranule according to the invention advantageously comprises an immediate microgranule to which is fixed a coating containing a coating agent which makes possible the controlled release of cisplatin and/or of other active principles, the said immediate microgranule being composed either of a mixture of excipients, of cisplatin and optionally of other active principles or of a neutral support grain coated with a mixture of excipients, of cisplatin and optionally of other active is principles.

Immediate microgranule is understood to mean a microgranule, the formulation excipients of which have no significant effect on the rate of release or of diffusion of the active principle.

The coating agent which makes possible the controlled release of cisplatin or optionally of other active principles is preferably composed of one or more pharmaceutically acceptable coating polymers chosen in particular from cellulose polymers or from methacrylic acid copolymers and preferably the poly(ethyl acrylate, methyl methacrylate)s sold under the trade name Eudragit NE 30D®.

The coating containing the coating agent described above is advantageously composed of a single polymer or optionally of a mixture of polymers and/or of a sequence of polymer layers.

Various conventional additives can optionally be combined with the polymer of the coating layer which provides for the controlled release, in particular: a lubricating agent and/or a plasticizing agent and/or a surface-active agent.

The lubricating agent can be composed of a conventional pharmaceutically acceptable lubricant, in particular talc.

The plasticizing agent is preferably composed of a pharmaceutically acceptable plasticizing agent chosen from aliphatic esters, such as esters of citric, phthalic and oxalic acids, and preferably triethyl citrate.

The surfactant can be of anionic, cationic, amphoteric or, preferably, non-ionic type, in particular the polysorbate 80 sold under the trade name Montanox 80®.

A so-called protective coating or prefixing layer can advantageously be applied between the immediate microgranule and the coating containing the coating agent, this inserted layer having the role of isolating the active principle from the polymer used in the coating described above.

The addition of sodium chloride to the mixture of excipients makes it possible to reinforce the stability of the cisplatin active principle. The mixture of excipients thus advantageously comprises sodium chloride.

The microgranules according to the invention advantageously contain a cisplatin content of between 25 and 350 mg/g and preferably between 50 and 60 mg/g.

The present invention also relates to the process for the preparation of the controlled-release microgranules containing cisplatin according to the invention.

The said process consists in fixing cisplatin to neutral support grains by spraying a fixing suspension containing cisplatin in aqueous/alcoholic medium, in alcoholic medium or in aqueous medium.

The fixing suspension is preferably aqueous and contains a stabilizing agent, such as sodium chloride, and one or more binding agents, such as hydroxypropylmethylcellulose or polyethylene glycol. A surface-active agent as described above can optionally be added to the fixing suspension.

The immediate microgranules, once coated with the coating agent which makes possible the controlled release of cisplatin, can be lubricated with talc.

The solvents used in the stages for the preparation of the microgranules of the present invention can be aqueous, alcoholic and/or aqueous/alcoholic in nature. Preferably, water will be used as sole solvent during the manufacturing process.

The microgranules according to the invention can be obtained by extrusion-spheronization by mixing, in a single stage, cisplatin, binding agents and stabilizing agents in aqueous medium.

The microgranules described in the present invention are obtained by use of any equipment appropriate for the preparation and the coating of microgranules well known to a person skilled in the art and in particular equipment of conventional pan, perforated pan, fluidized air bed, extruder and spheronizer type.

Another subject of the present invention is a pharmaceutical preparation containing the controlled-release cisplatin microgranules according to the invention, optionally obtained according to the process described above, in an amount which makes it possible to obtain a unit dose of between 10 and 50 mg of cisplatin.

The said pharmaceutical preparation preferably contains a mixture of controlled-release cisplatin microgranules and of an anticancer agent, for example fluorouracil, S1, the combination of vinblastine with bleomycin, the combination of etoposide with bleomycin, or paclitaxel, as combination product for a use in anticancer therapy which is simultaneous, separate or spread out over time.

Finally, the present invention relates to the use of the microgranules according to the invention in manufacturing a medicament, to be administered by the oral route, intended to be used at low doses, in particular less than or equal to approximately 20 mg/m$^2$/day.

The said medicament can advantageously be used in polychemotherapy and/or in combination with a radiotherapy in order to obtain an average cisplatin blood concentration of between 0.5 and 1.0 µg/ml.

The following examples illustrate the invention without limiting the scope thereof. The percentages are expressed by mass, except when otherwise indicated.

EXAMPLE 1

Protocol for the preparation of immediate microgranules by fixing cisplatin to neutral grains.

Preparation of the Fixing Suspension

The fixing excipients are weighed in the appropriate proportions for an amount of cisplatin of 100 g, The solvent or the solvent mixture is placed in a container with stirring, The binder or the mixture of binders is slowly added and the mixture is stirred until a homogeneous solution is obtained, The active principle is added at the time of fixing and the mixture is stirred until a homogeneous suspension is obtained.

Fixing of the Active Principle to the Neutral Support Grains

The necessary amount of Neutres 20® (sold by the company Np-pharm, the mean particle size of which is between 0.7 and 0.9 mm, composed of 75% sucrose and 25% maize starch) is placed in the device used for fixing the active principle.

The active principle is fixed to the Neutres 20® by continuous spraying of the suspension described above, The mass of microgranules obtained is sieved,

EXAMPLE 2
Preparation of Immediate Microgranules A

The following fixing excipients are weighed, in the proportions shown, for an amount of cisplatin of 100 g

| | | |
|---|---|---|
| PEG 4000 | 18 g | 75% of the content on a dry basis |
| PHARMACOAT 603 ® | 9 g | 25% of the content on a dry basis |
| PURIFIED WATER | 10 g | 5% of the solvent |
| 95% ETHYL ALCOHOL | 190 g | 95% of the solvent |

Final formula:

| | |
|---|---|
| CISPLATIN | 22.3% |
| NEUTRES 20 ® | 72.4% |
| PEG 4000 | 4.0% |
| PHARMACOAT 603 ® | 1.3% |
| THEORETICAL CONTENT | 223 mg/g |

EXAMPLE 3
Preparation of Immediate Microgranules B

The following fixing excipients are weighed, in the proportions shown, for an amount of cisplatin of 100 g

| | | |
|---|---|---|
| PEG 4000 | 18.2 g | 30.5% of the content on a dry basis |
| PHARMACOAT 603 ® | 6.0 g | 10.1% of the content on a dry basis |
| SODIUM CHLORIDE | 30.2 g | 50.7% of the content on a dry basis |
| MONTANOX 80 ® | 5.2 g | 8.7% of the content on a dry basis |
| PURIFIED WATER | 303.0 g | 100% of teh solvent |

Final formula:

| | |
|---|---|
| CISPLATIN | 5.5% |
| NEUTRES 20 ® | 91.3% |
| PEG 4000 | 1.0% |
| PHARMACOAT 603 ® | 0.3% |
| MONTANOX 80 ® | 0.3% |
| SODIUM CHLORIDE | 1.6% |
| THEORETICAL CONTENT | 55 mg/g |

EXAMPLE 4
Preparation of Immediate Microgranules C

The following fixing excipients are weighed, in the proportions shown, for an amount of cisplatin of 100 g

| | | |
|---|---|---|
| PEG 4000 | 18.0 g | 28.0% of the content on a dry basis |
| PHARMACOAT 603 ® | 6.0 g | 9.4% of the content on a dry basis |
| SODIUM CHLORIDE | 30.0 g | 46.7% of the content on a dry basis |
| MONTANOX 80 ® | 10.2 g | 15.9% of the content on a dry basis |
| PURIFIED WATER | 302.2 g | 100% of the solvent |

Final formula:

| | |
|---|---|
| CISPLATIN | 5.4% |
| NEUTRES 20 ® | 91.0% |
| PEG 4000 | 1.0% |
| PHARMACOAT 603 ® | 0.3% |
| MONTANOX 80 ® | 0.7% |
| SODIUM CHLORIDE | 1.6% |
| THEORETICAL CONTENT | 54 mg/g |

EXAMPLE 5
Preparation of Immediate Microgranules D

The following fixing excipients are weighed, in the proportions shown, for an amount of cisplatin of 100 g

| | | |
|---|---|---|
| PEG 4000 | 18.0 g | 28.0% of the content on a dry basis |
| PHARMACOAT 603 ® | 6.0 g | 9.4% of the content on a dry basis |
| SODIUM CHLORIDE | 30.0 g | 46.7% of the content on a dry basis |
| MONTANOX 80 ® | 10.2 g | 15.9% of the content on a dry basis |
| PURIFIED WATER | 299.6 g | 100% of the solvent |

Final formula:

| | |
|---|---|
| CISPLATIN | 5.4% |
| NEUTRES 20 ® | 91.0% |
| PEG 4000 | 1.0% |
| PHARMACOAT 603 ® | 0.3% |
| MONTANOX 80 ® | 0.6% |
| SODIUM CHLORIDE | 1.7% |
| THEORETICAL CONTENT | 54 mg/g |

EXAMPLE 6
Preparation of Immediate Microgranules E

The following fixing excipients are weighed, in the proportions shown, for an amount of cisplatin of 100 g

| | | |
|---|---|---|
| PEG 4000 | 18 g | 72% of the content on a dry basis |
| PHARMACOAT 603 ® | 6 g | 24% of the content on a dry basis |
| SODIUM CHLORIDE | 1 g | 4% of the content on a dry basis |
| PURIFIED WATER | 240 g | 100% of the solvent |

Final formula:

| | |
|---|---|
| CISPLATIN | 5.5% |
| NEUTRES 20 ® | 93.1% |
| PEG 4000 | 1.0% |
| PHARMACOAT 603 ® | 0.3% |
| SODIUM CHLORIDE | 0.1% |
| THEORETICAL CONTENT | 55 mg/g |

EXAMPLE 7
Protocol for the Preparation of Sustained release microgranules

Preparation of the Coating Suspension

The coating excipients are weighed in the appropriate proportions,

The solvent or the mixture of solvents is placed in a container with stirring,

The coating agent or the mixture of coating agents is slowly added and the mixture is stirred until a homogeneous solution is obtained, The various additives are slowly added and the mixture is stirred until a homogeneous suspension is obtained, Stirring is continued throughout the coating phase.

Coating the Microgranules

A fraction of the immediate microgranules obtained according to the protocol of Example 1 is placed in the equipment used for the coating, The microgranules are coated by continuous spraying of the suspension described above, The mass of microgranules obtained is sieved, The microgranules are dried at ambient temperature, This sequence of operations is repeated the necessary number of times to produce the desired kinetics.

EXAMPLE 8

Preparation of Sustained-release Microgranules A1

The following coating excipients are weighed in the proportions shown

| | | |
|---|---|---|
| EUDRAGIT L 30 D ® | 10.0 g | Eudragit ® content on a dry basis = 30% of the weighed mass of Eudragit ® |
| TRIETHYL CITRATE | 0.3 g | Content on a dry basis of TRIETHYL CITRATE = 10% of content on a dry basis of Eudragit ® |
| PURIFIED WATER | 5.0 g | Dilution solvent = 50% of the weighed mass of Eudragit ® |

The immediate microgranules A of Example 2 are coated

Final formula:

| | |
|---|---|
| CISPLATIN | 18.2% |
| NEUTRES 20 ® | 59.1% |
| PEG 4000 | 3.3% |
| PHARMACOAT 603 ® | 1.1% |
| EUDRAGIT L 100-55 ® | 0.8% |
| EUDRAGIT L 30 D ® | 10.2% |
| EUDRAGIT NE 30 D ® | 1.0% |
| TRIETHYL CITRATE | 1.0% |
| TALC | 5.3% |
| THEORETICAL CONTENT | 182 mg/g |

EXAMPLE 9

Preparation of Sustained-release Microgranules A2

The following coating excipients are weighed in the proportions shown

| | | |
|---|---|---|
| EUDRAGIT S 100 ® | 12.0 g | |
| 17 g/l concentrated aqueous ammonia solution | 6.1 g | Content on a dry basis of ammonia 0.85% of the content on a dry basis on Eudragit ® |
| TRIETHYL CITRATE | 6.0 g | Content on a dry basis of TRIETMYL CITRATE = 50% of the content on a dry basis of Eudragit ® |
| TALC | 4.0 g | Content on a dry basis of TALC ⅓ of the content on a dry basis of Eudragit ® |
| PURIFIED WATER | 35.9 g | Dilution solvent = 50% of the weighed mass of Eudragit ® |

The immediate microgranules A of Example 2 are coated

Final formula:

| | |
|---|---|
| CISPLATIN | 20.7% |
| NEUTRES 20 ® | 67.2% |
| PEG 4000 | 3.8% |
| PHARMACOAT 603 ® | 1.2% |
| EUDRAGIT S 100 ® | 3.77% |
| AMMONIA | 0.03% |
| TRIETHYL CITRATE | 1.4% |
| TALC | 1.9% |
| THEORETICAL CONTENT | 207 mg/g |

EXAMPLE 10

Preparation of Sustained-release Microgranules E1

The following coating excipients are weighed in the proportions shown

| | | |
|---|---|---|
| EUDRAGIT L 30 D ® | 10.0 g | Content on a dry basis of Eudragit ®= 30% of the weighed mass of Eudragit ® |
| TRIETHYL CITRATE | 0.3 g | Content on a dry basis of TRIETHYL CITRATE = 10% of the content on a dry basis of Eudragit ® |
| PURIFIED WATER | 5.0 g | Dilution solvent = 50% of the weighed mass of Eudragit ® |

The immediate microgranules E of Example 6 are coated

Final formula:

| | |
|---|---|
| CISPLATIN | 4.5% |
| NEUTRES 20 ® | 75.35% |
| PEG 4000 | 0.8% |
| PHARMACOAT 603 ® | 0.3% |
| SODIUM CHLORIDE | 0.05% |
| EUDRAGIT L 30 ® | 9.0% |
| TRIETHYL CITRATE | 0.9% |
| TALC | 9.1% |
| THEORETICAL CONTENT | 45 mg/g |

EXAMPLE 11

Preparation of Sustained-release Microgranules E2

The following coating excipients are weighed in the proportions shown

| | | |
|---|---|---|
| EUDRAGIT NE 30 D ® | 10.0 g | Content on a dry basis of Eudagit ® = 30% of the weighed mass of Eudragit ® |
| PURIFIED WATER | 5.0 g | Dilution solvent = 50% of the weighed mass of Eudragit ® |

The immediate microgranules E of Example 6 are coated

Final formula:

| | |
|---|---|
| CISPLATIN | 5.4% |
| NEUTRES 20 ® | 91.3% |
| PEG 4000 | 0.95% |
| PHARMACOAT 603 ® | 0.3% |
| SODIUM CHLORIDE | 0.05% |
| EUDRAGIT NE 30 D ® | 1.0% |

-continued

| TALC | 1.0% |
|---|---|
| THEORETICAL CONTENT | 54 mg/g |

EXAMPLE 12

Preparation of Sustained-release Microgranules E3

The following coating excipients are weighed in the proportions shown

| EUDRAGIT NE 30 D ® | 10.0 g | Content on a dry basis of Eudragit ® = 30% of the weighed mass of Eudragit ® |
|---|---|---|
| PURIFIED WATER | 5.0 g | Dilution solvent = 50% of the weighed mass of Eudragit ® |

The immediate microgranules E of Example 6 are coated
Final formula:

| CISPLATIN | 5.3% |
|---|---|
| NEUTRES 20 ® | 89.6% |
| PEG 4000 | 0.95% |
| PHARMACOAT 603 ® | 0.3% |
| SODIUM CHLORIDE | 0.05% |
| EUDRAGIT NE 30 D ® | 1.9% |
| TALC | 1.9% |
| THEORETICAL CONTENT | 53 mg/g |

EXAMPLE 13

Preparation of Sustained-release Microgranules E4

The following coating excipients are weighed in the proportions shown

| EUDRAGIT NE 30 D ® | 10.0 g | Content on a dry basis of Eudragit ® = 30% of the weighed mass of Eudragit ® |
|---|---|---|
| TALC | 3.0 g | Content on a dry basis of TALC = 100% of the content on a dry basis of Eudragit ® |
| PURIFIED WATER | 5.0 g | Dilution solvent = 50% of the weighed mass of Eudragit ® |

The following coating excipients are weighed in the proportions shown

| EUDRAGIT L NE 30 D ® | 10.0 g | Content on a dry basis of Eudragit ® = 30% of the weighed mass of Eudragit ® |
|---|---|---|
| TALC | 3.0 g | Content on a dry basis of TALC = 100% of the content on a dry basis of Eudragit ® |
| TRIETHYL CITRATE | 0.3 g | Content on a dry basis of TRIETHYL CITRATE = 10% of the content on a dry basis of Eudragit ® |
| PURIFIED WATER | 5.0 g | Dilution solvent = 50% of the weighed mass of Eudragit ® |

The immediate microgranules E of Example 6 are coated
Final formula:

| CISPLATIN | 4.4% |
|---|---|
| NEUTRES 20 ® | 74.8% |
| PEG 4000 | 0.8% |
| PHARMACOAT 603 ® | 0.3% |
| SODIUM CHLORIDE | 0.04% |
| EUDRAGIT NE 30 D ® | 0.8% |
| EUDRAGIT L 30 D ® | 8.56% |
| TRIETHYL CITRATE | 0.9% |
| TALC | 9.4% |
| THEORETICAL CONTENT | 44 mg/g |

Preclinical and Clinical Studies

Bioavailability in Animals

The bioavailability of cisplatin microgranules is compared either with that of cisplatin administered conventionally by the I.V. route (absolute bioavailability) or with that of the injectable formulation administered by the oral route (relative bioavailability) in the dog, the rat and the monkey after single or repeated administration (1 daily administration for 7 days).

Blood samples are taken 15 min, 30 min, 1, 2, 4, 8 and 24 hours after the oral or I.V. administration of cisplatin. The total plasma platinum concentration is determined by spectrophotometric atomic absorption. The mean of the results obtained as regards the absolute bioavailability and the relative bioavailability are combined in Tables 1 and 2 below.

TABLE 1

ABSOLUTE BIOAVAILABILITY

|  | A | A1 | IV CDDP administered by the oral route | E2 | E3 |
|---|---|---|---|---|---|
| Dog – n = 3 1 mg/kg (20 mg/m$^2$) | 63.4% | 46.0% | 47.3% | 66.1% | 49.0% |
| Monkey – n = 3 1 mg/kg | 17.3% | 11.4% | 8.0% | 13.7% | 7.7% |
| Rat – n = 3 1 mg/kg (6 mg/m$^2$) | 47.7% | 41.9% | 44.2% | | |

TABLE 2

RELATIVE BIOAVAILABILITY WITH RESPECT TO THE INJECTABLE FORMULATION ADMINISTERED PER OS IN THE RAT

|  | E | E1 | E2 | E3 | E4 |
|---|---|---|---|---|---|
| Single administration 2 mg/kg (12 mg/m$^2$) n = 4 | 117% | 118% | 138% | 69% | 163% |
| Repeated administration 0.5 mg/kg/day (3 mg/m$^2$/day) for 7 days n = 5 | 173% | 249% | 206% | 164% | 128% |

Moreover, the residual plasma cisplatin concentrations are measured in the rat after administration of the formulations described in the present invention, in comparison with the injectable formulation administered per os, at the rate of 2 mg/kg/day (12 mg/m$^2$/day) for 7 consecutive days with a single daily intake. The results are illustrated by the curves presented in the appendix, FIGS. 1 and 2.

FIG. 1 represents the plasma cisplatin concentration, as a function of time, of five groups of five rats to which have been respectively administered 2 mg/kg/day (12 mg/m$^2$/day) of microgranules E, E2, E3 and E4 by the oral route and injectable cisplatin administered per os for 7 consecutive days at the rate of a single intake per day. The plasma cisplatin concentration is measured 24 hours after each administration.

FIG. 2 represents the plasma cisplatin concentration, as a function of time, of three groups of five rats to which have been respectively administered microgranules B and C by the oral route and injectable cisplatin administered per os under the same conditions as those in FIG. 1.

These combined results show that:
- the digestive absorption of the cisplatin microgranule oral formulations according to the invention is superior to that of the injectable formulation administered per os in all the species tested, whether after single or repeated administration,
- the plasma platinum concentrations measured after administration of the cisplatin microgranules according to the invention are more sustained than those obtained after oral administration of an equivalent dose of an injectable formulation.

Acute Toxicology and Histopathology in Dogs of the Beagle Breed Treated with Microgranules E2

The objective of this study is to determine the maximum tolerated dose (MTD) of cisplatin microgranules E2 in the dog after the administration of a single dose. A total of 6 male dogs and 6 female dogs is used. Doses of 0.2, 0.5, 1.0 and 2.0 mg/kg (4, 10, 20 and 40 mg/m$^2$) of cisplatin microgranules by the oral route and a dose of 1 mg/kg (20 mg/m$^2$) of cisplatin of trademark Cisplatyl® by the intravenous route are adminis-tered to the animals.

The plasma platinum concentration is measured 30 min, 1, 4 and 24 hours after administration. Histopathological examination is carried out at the end of the 14th day The animals to which 1 or 2 mg/kg (20 or 40 mg/m$^2$) of cisplatin microgranules and 1 mg/kg of I.V. cisplatin have been administered suffered from vomiting. Cases of diarrhoea were recorded in the animals treated with 1 mg/kg of I.V. cisplatin and 2 mg/kg of cisplatin microgranules. The 2 mg/kg oral dose of cisplatin microgranules also caused a loss in weight, a decrease in food intake, a decrease in weight of the spleen and thymus, a duodenal ulcer in one dog and slight renal lesions.

Histopathological examination shows that virtually all the animals treated with 1.0 mg/kg and 2.0 mg/kg of cisplatin microgranules suffer from moderate hypoplasia of the bone marrow. Intensity of hypoplasia depends on the dose of cisplatin administered.

The 1 mg/kg oral dose of cisplatin microgranules induces toxic effects to a lesser extent than the 1 mg/kg dose of I.V. cisplatin. Moreover, these toxic effects are not irreversible.

The lower doses of cisplatin microgranules administered by the oral route are particularly well tolerated and only changes of little importance are noticed in the intestine.

The maximum tolerated dose (MTD) of cisplatin microgranules E2 in the dog after administration of a single dose thus lies between 1.0 mg/kg and 2.0 mg/kg. The absolute bioavailability of platinum lies between 41 and 77% (mean 64%). Moreover, the inter-animal variability is very low as regards the maximum plasma concentrations.

Subacute Toxicology in Dogs of the Beagle Breed After Administration of Repeated Doses of Cisplatin Microgranules E2

Zero (empty hard gelatin capsules, 0.25 and 1.0 mg/kg/day doses of cisplatin microgranules are administered to male dogs (3 per group) over a period of 4 weeks.

The weight of the dogs is monitored twice weekly and food and water intake is checked once weekly. Biochemical and haematological examinations of the blood and of the urine are carried out before and after the experimentation. The blood platinum concentrations are measured once weekly by spectrometric atomic absorption.

Histopathological and macroscopic examination is carried out at the end of the experimentation.

In the 1.0 mg/kg (20 mg/m$^2$) group:

The autopsy shows haemorrhagic lesions of the pylorus, of the duodenum and of the ileocaecal region of the colon.

Histopathological examination shows that virtually all the animals treated with 1.0 mg/kg of cisplatin microgranules suffer from pronounced hypoplasia of the bone marrow, from erosion in the gastrointestinal region, from granular degeneration of the renal tubules and from necrotic lesions of the testicles.

In the 0.25 mg/kg (5 mg/m$^2$) group

General tolerance is satisfactory throughout the duration of the treatment, with a slight reduction in food intake. Histopathological examination reveals a slight hypoplasia of the bone marrow.

Absolute Bioavailability in Man of Microgranules E2

Eight patients suffering from cancer of such a nature as to be sensitive to cisplatin receive, under randomization conditions, a single dose of 10 mg/m$^2$ of cisplatin, either orally in the form of microgranules E2 (hard gelatin capsules containing 2.5 and 5 mg) or by intravenous perfusion for 30 minutes (Cisplatyl® Bellon).

The total plasma platinum levels are measured before administration of the medicaments and then 15 min, 30 min, 45 min, 1h, 1h 30, 2h, 4h, 8h, 12h and 24h after administration of the medicaments.

Eight patients received the microgranules E2 and eight other patients received Cisplatyl® Bellon by the intravenous route. The mean value of the absolute bioavailability of cisplatin microgranules E2 is 39%. The variability between individuals after administration of microgranules E2 is moderate and similar to that observed after administration of I.V. Cisplatyl® (CV% =27.4% p.o. and 23.7% I.V. respectively).

What is claimed is:

1. Controlled-release microgranules comprising (1) (a) a mixture comprising cisplatin and at least one pharmaceutically acceptable excipient or (b) a core of a neutral support grain coated with a mixture comprising cisplatin and at least one pharmaceutically acceptable excipient; and (2) a coating fixed to the microgranule, wherein the coating comprises a coating agent which enables the controlled release of the mixture;

wherein the microgranules have a mean particle size of between 0.4 and 1.5 mm;

and wherein the microganules contain only cisplatin as an active ingredient.

2. The controlled-release microgranules of claim 1, wherein the coating agent is a cellulose polymer or a methacrylic acid polymer.

3. The controlled-release microgranules of claim 2, wherein the coating agent is a poly(ethyl acrylate, methyl acrylate).

4. The controlled-release microgranules of claim 1, wherein the coating agent consists of a single polymer, or a mixture of polymers.

5. The controlled-release microgranules of claim 1, wherein the coating comprises one or more polymer layers.

6. The controlled-release microgranules of claim 1, wherein the coating further comprises a lubricating agent combined with the coating agent.

7. The controlled-release microgranules of claim 6, wherein the lubricating agent is talc.

8. The controlled-release microgranules of claim 1, wherein the coating further comprises a plasticizing agent combine with the coating agent.

9. The controlled-release microgranules of claim 8, wherein the plasticizing agent is triethyl citrate.

10. The controlled-release microgranules of claim 1, wherein the coating further comprises a surface active agent combined with the coating agent.

11. The controlled-release microgranules of claim 10, wherein the surface active agent is polysorbate 80.

12. The controlled-release microgranules of claim 1, wherein the coating further comprises a lubricating agent, a plasticizing agent, and a surface active agent combined with the coating agent.

13. The microgranules of claim 1, further comprising a protective coating layer fixed in between the microgranule core and the coating.

14. The controlled-release microgranules of claim 1, wherein the excipient comprises sodium chloride.

15. The controlled-release microgranules of claim 1, having a cisplatin content of between 25 and 350 mg of cisplatin per gram of microgranules.

16. The controlled-release microgranules of claim 15, wherein the cisplatin content is between 50 and 60 mg of cisplatin per gram of microgranules.

17. A process for preparing the microgranules of claim 1, which comprises spraying cisplatin in a suspension medium onto a neutral support grain to form microgranules, and then fixing a coating to the microgranules, wherein the suspension medium is water, an alcohol, or a water-alcohol mixture.

18. The process of claim 17, wherein the suspension medium further comprises a stabilizing agent, a binding agent, and a surface active agent.

19. The process of claim 18, wherein the stabilizing agent is sodium chloride.

20. The process of claim 18, wherein the binding agent is hydroxypropylmethylcellulose or polyethylene glycol.

21. The process of claim 18, wherein the microgranule is coated with a coating agent.

22. The process of claim 18, wherein the coating further comprises a lubricating agent combined with the coating agent.

23. The process of claim 22, wherein the lubricating agent is talc.

24. A pharmaceutical composition comprising a microgranule according to claim 1, having a unit dose of between 10 and 50 mg.

25. A method for manufacturing an oral medicament, comprising preparing microgranules according to claim 1 and formulating an oral medicament comprising said microgranules.

26. A method for treating cancer comprising administering to a subject in need thereof the oral medicament according to claim 25 at a daily cisplatin dosage of not more than 20 mg/m$^2$.

27. The method according to claim 26, in combination with administering to the subject at least one other chemotherapy agent.

28. A method for treating cancer comprising administering to a subject in need thereof the oral medicament according to claim 26, in combination with a radiotherapy treatment.

29. The method according to claim 26, wherein the average blood cisplatin concentration of said patient is maintained at a level between 0.5 and 1.0 µg/ml.

30. The controlled-release microgranules of claim 1, wherein the mean particle size of said microgranules is between 1 and 1.25 mm.

* * * * *

UNITED STATES PATENT AND TRADEMARK OFFICE
CERTIFICATE OF CORRECTION

PATENT NO. : 6,458,389 B1
DATED : October 1, 2002
INVENTOR(S) : Patrice Debregeas et al.

It is certified that error appears in the above-identified patent and that said Letters Patent is hereby corrected as shown below:

Column 7,
Example 9, please insert -- = -- after "TALC" and before "$^1/_3$";

Column 9,
Example 13, please delete the term "NE" after "EUDRAGIT L";

Column 12,
Lines 61-62, please change "methyl acrylate" to -- methacrylate --.

Column 13,
Line 8, please change "combine" to -- combined --.

Signed and Sealed this

Nineteenth Day of October, 2004

JON W. DUDAS
*Director of the United States Patent and Trademark Office*